(12) United States Patent
Murthy Aravalli et al.

(10) Patent No.: US 10,758,398 B2
(45) Date of Patent: Sep. 1, 2020

(54) APPARATUS AND ASSOCIATED METHODOLOGIES FOR CREATING A STOMA

(71) Applicant: Covidien LP, Mansfield, MA (US)

(72) Inventors: Avvln Srinivasa Murthy Aravalli, Andhra Pradesh (IN); Amarsinh Deeliprao Jadhav, Andhra Pradesh (IN); Rajat Ravindra Rokde, Maharashtra (IN)

(73) Assignee: COVIDIEN LP, Mansfield, MA (US)

( * ) Notice: Subject to any disclaimer, the term of this patent is extended or adjusted under 35 U.S.C. 154(b) by 414 days.

(21) Appl. No.: 15/705,337

(22) Filed: Sep. 15, 2017

(65) Prior Publication Data

US 2018/0116860 A1  May 3, 2018

Related U.S. Application Data

(60) Provisional application No. 62/415,597, filed on Nov. 1, 2016.

(51) Int. Cl.
*A61F 5/445* (2006.01)
*A61F 5/449* (2006.01)
(Continued)

(52) U.S. Cl.
CPC ............ *A61F 5/445* (2013.01); *A61B 17/064* (2013.01); *A61B 17/1114* (2013.01);
(Continued)

(58) Field of Classification Search
CPC .......... A61F 5/445; A61F 4/445; A61F 5/449; A61F 2005/4455; A61B 17/064; A61B 17/1114; A61B 5/6849
See application file for complete search history.

(56) References Cited

U.S. PATENT DOCUMENTS 4,217,664 A * 8/1980 Faso ............... A61F 2/0063
600/32
4,351,322 A * 9/1982 Prager ............ A61F 5/4404
600/32

(Continued)

OTHER PUBLICATIONS

U.S. Appl. No. 62/521,755, inventor Srinivasa Murthy Aravalli.
U.S. Appl. No. 62/541,958, inventor Srinivasa Murthy Aravalli.

*Primary Examiner* — Adam Marcetich
*Assistant Examiner* — Jessica R Arble

(57) ABSTRACT

A guide apparatus for facilitating formation of a stoma includes a guide having an outer flange segment arranged about a central longitudinal axis and an insert segment. The flange segment is configured for engaging end margins of a body vessel extending through an opening in skin of a subject, and defines a plurality of apertures. The insert segment extends from the outer flange segment along the longitudinal axis. The insert segment is configured for at least partial positioning within the body vessel to maintain the patency of the body vessel. The guide apparatus further includes a plurality of fasteners for insertion within respective apertures of the flange segment of the guide. The fasteners are configured for penetrating the end margins of the body vessel extending through the opening in the skin to attach the end margins to the skin to thereby create a stoma.

12 Claims, 7 Drawing Sheets

(51) Int. Cl.
*A61B 17/064* (2006.01)
*A61B 17/11* (2006.01)
A61B 17/00 (2006.01)
A61B 17/115 (2006.01)

(52) U.S. Cl.
CPC ........... *A61F 5/449* (2013.01); *A61B 17/1155* (2013.01); *A61B 2017/00004* (2013.01); *A61B 2017/0647* (2013.01); *A61B 2017/0648* (2013.01); *A61B 2017/0649* (2013.01); *A61B 2017/1135* (2013.01); *A61F 2005/4455* (2013.01)

(56) References Cited

U.S. PATENT DOCUMENTS

| | | | |
|---|---|---|---|
| 7,708,684 B2* | 5/2010 | Demarais | A61B 17/0401 600/37 |
| 8,257,365 B2* | 9/2012 | Demarais | A61B 17/0057 606/139 |
| 2003/0040749 A1* | 2/2003 | Grabowski | A61B 17/7059 606/71 |
| 2005/0033240 A1* | 2/2005 | Oishi | A61J 15/0015 604/174 |
| 2008/0154355 A1* | 6/2008 | Benichou | A61F 2/2415 623/1.26 |
| 2012/0123361 A1* | 5/2012 | Johansson | A61F 5/445 604/337 |
| 2013/0030397 A1* | 1/2013 | Sabeti | A61F 5/445 604/335 |

* cited by examiner

APPARATUS AND ASSOCIATED METHODOLOGIES FOR CREATING A STOMA

CROSS-REFERENCE TO RELATED APPLICATIONS

This application claims the benefit of and priority to U.S. Provisional Patent Application No. 62/415,597 filed Nov. 1, 2016, the entire disclosure of which is incorporated by reference herein.

TECHNICAL FIELD

The present disclosure generally relates to a surgical apparatus and associated method for establishing a stoma, and, in particular, relates to a guide apparatus for effectively securing the end margins of an intestine about an opening in an abdominal wall in conjunction with stoma formation in an ostomy procedure.

BACKGROUND

Exteriorization of an internal body vessel such as the intestine is called a stoma. Stomas may be created in conjunction with an ostomy procedure by suturing a bisected portion of an intestine to the abdominal wall to provide internal access into the intestine for collecting fecal matter. Complications associated with stomas can include leaks, bleeding, parastomal herniation, necrosis, stenosis, retraction, dermal infection, mucocutaneous separation, prolapse, diversion colitis, etc. Thus, a need exists to develop apparatuses and methods for reducing risks and complications associated with stoma formation, and to provide uniform connection of the bisected portion to the abdominal wall.

SUMMARY

Accordingly, a guide apparatus for facilitating formation of a stoma includes a guide having an outer flange segment arranged about a central longitudinal axis and an insert segment. The flange segment is configured for engaging end margins of a body vessel extending through an opening in skin of a subject, and defines a plurality of apertures. The insert segment extends from the outer flange segment. The insert segment is configured for at least partial positioning within the body vessel to maintain the patency of the body vessel. The guide apparatus further includes a plurality of fasteners for insertion within respective apertures of the flange segment of the guide. The fasteners are configured for penetrating the end margins of the body vessel extending through the opening in the skin to attach the end margins to the skin to thereby create a stoma.

In embodiments, the fasteners each include a head segment and an elongated fastener segment depending from the head segment. The head segments each define a cross-sectional dimension less than a corresponding cross-sectional dimension of the apertures of the flange segment of the guide to permit the guide to be removed subsequent to application of the fasteners by passage of the head segments through the apertures.

In some embodiments, the fasteners are arranged within the flange segment whereby adjacent fasteners are in equidistant spaced relation. The fasteners each may include anchoring structure configured to facilitate securement of each fastener to the end margins of the body vessel and the skin.

In certain embodiments, the fasteners may be one of an elongated pin, a tack or a staple. The fasteners may comprise a biodegradable material.

In embodiments, the insert segment of the guide is separable from the flange segment. In some embodiments, at least the flange segment of the guide comprises a biodegradable material.

In an embodiment, a method for facilitating formation of a stoma includes:

accessing an internal body vessel through an opening in a skin of a subject;

positioning end margins of the body vessel against the skin surrounding the opening;

applying a flange segment of a guide against the end margins of the body vessel; and delivering fasteners through apertures extending through the flange segment of the guide to secure the end margins of the body vessel to the skin and form a stoma.

In some embodiments, the method includes introducing an insert segment of the guide into the body vessel to maintain a patency of the body vessel.

The method may include removing the guide. In certain embodiments, the fasteners each include a head segment and an elongated fastener segment depending from the head segment. The head segments each define a cross-sectional dimension less than a corresponding cross-sectional dimension of the apertures of the flange segment of the guide whereby, during removing the guide, the head segments of the fasteners pass through the apertures of the flange segment of the guide.

In some embodiments, the internal body vessel is an intestine.

In an embodiment, a method for facilitating formation of a stoma includes:

accessing an internal body vessel through an opening in a skin of a subject;

positioning end margins of the body vessel against the skin surrounding the opening; and delivering a staple through the end margins to secure the end margins of the body vessel to the skin and create a stoma.

In some embodiments, the method includes introducing an anvil beneath the skin and wherein delivering the staple includes advancing the staple to at least partially crimp legs of the staple with the anvil. Advancing the staple may include advancing a plurality of staples arranged in an annular array through the end margins of the body vessel and the skin.

In embodiments, the body vessel is an intestine.

The guide apparatus of the present disclosure provides a template for positioning against end margins of a body vessel, e.g., the intestine, for uniform delivery of fasteners within the end margins to facilitate the formation of a stoma. The stoma established with the guide apparatus minimizes the issues associated with conventional suture created stoma methodologies including necrosis, dislodgement, prolapse, stenosis and mucocutaneous separation. The guide apparatus eliminates operator error, maintains the patency of the body vessel, and is easily removed subsequent to formation and connection of the body vessel to the skin. Additional methodologies of stoma creation with or without the guide apparatus disclosed herein provide flexibility to the clinician and may be effected with conventional fastener and stapling apparatuses.

Other features of the present disclosure will be appreciated from the following description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

The following discussion of the surgical guide apparatus will focus on in its application in facilitating formation of a stoma in an ostomy procedure, particularly, in securing the end margins of an intestine to the abdominal tissue in connection with a colostomy or ileostomy procedure. However, the guide apparatus has application in other ostomy procedures including ileostomy, urostomy, gastrostomy and jejunostomy procedures.

Figure 1:
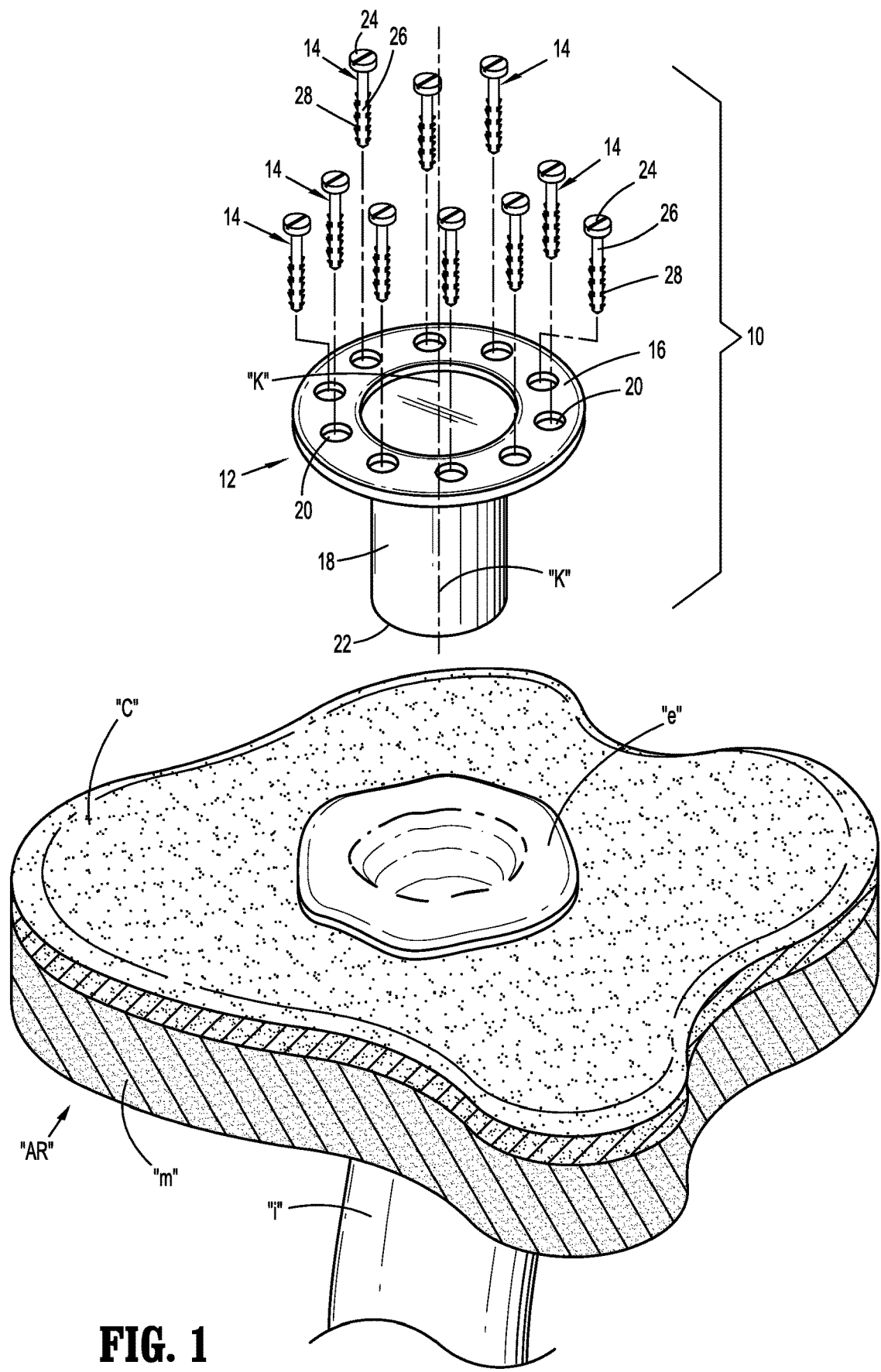
FIG. 1 is a perspective view of the guide apparatus for facilitating formation of a stoma within abdominal tissue illustrating the guide and the fasteners introducible within the guide.

Referring to FIG. 1, an abdominal region "AR" of a subject's body generally includes abdominal tissue having an outer cutaneous layer "c" (e.g., epidermis, dermis, and hypodermis) and an inner muscle or tissue layer "m" (e.g., anterior rectus sheath) that enshroud organs, vessels, and/or other tissue for performing various bodily functions such as digestion. For instance, as the part of a digestive system of a subject's body, the stomach and the intestines are supported in the abdominal region. In the course of a natural digestion process, the stomach and the intestines collaborate with the rest of the digestive system to process food and excrete fecal matter through the anus. Unfortunately, as a result of disease or injury to the intestines, it may become necessary to bypass natural digestion by providing an artificial stoma through the abdominal region in order to safely excrete the fecal matter from the subject's body. To create the stoma, the end margins "e" of the intestine or colon "i" are advanced through an opening in the abdomen formed via a scalpel or the like and at least partially flared outwardly to circumscribe the opening. In a conventional ostomy procedure, the end margins "e" would be sutured to the cutaneous layer "c" and the underlying muscle layer "m" to create the stoma and effect the colostomy.

FIG. 1 illustrates the guide apparatus 10 utilized to secure the end margins "e" of the intestine "i" relative to the abdominal region "AR" of the abdominal cavity. The guide apparatus 10 includes a guide 12 and a plurality of fasteners 14. The guide 12 includes an outer flange segment 16 coaxially arranged about a central longitudinal axis "k" and an insert segment 18 depending from the flange segment 16 and extending along the central axis "k". The flange segment 16 defines a plurality of apertures 20 therethrough for reception of the fasteners 14. In embodiments, the apertures 20 are also coaxially arranged about the central axis "k" with adjacent apertures 20 being radially spaced at predefined radial distances. The radial distances are equal such that the apertures 20 are equidistally spaced about the flange segment 16, and, as a consequence, the fasteners 14 are evenly applied within the end margins "e". This facilitates healing and establishment of the stoma, and minimizes the potential of the aforedescribed complications including leaking, dermal infection, parastomal herniation, etc.

The insert segment 18 is configured for insertion within the intestine "i" to maintain the patency of the intestine "i" during application of the fasteners 14 and formation of the stoma. In embodiments, the insert segment 18 is generally cylindrical-shaped and may possess a rounded entry end 22 to facilitate insertion within the lumen of the intestine "i". The insert segment 18 may be solid or alternatively hollow. The insert segment 18 may be coaxially arranged about the central axis "k" or obliquely arranged with respect to the central longitudinal axis "k".

The fasteners 14 may be in the form of a surgical tack or pin with each fastener 14 defining a head segment 24 and an elongated pin-shaped fastener segment 26. The fastener segments 26 each may include anchoring structure, e.g., barbs 28, to assist in engaging tissue and retaining the fasteners 14 within the end margins "e", cutaneous tissue "c" and the underlying muscle tissue "m". The barbs 28 may be pointed and exhibit some flexibility, or, alternatively, be rigid. The fastener segments 26 are dimensioned for insertion within the apertures 20 of the flange segment 16. In embodiments, the head segment 24 of each fastener 14 defines a cross-sectional dimension or diameter less than the internal dimension or diameter of the apertures 20 such that the head segments 24 may also pass through the apertures 20. This facilitates removal of the guide 12 subsequent to securement of the fasteners 14 and stoma formation. The fasteners 14 may be formed from any biocompatible material including stainless steel, titanium or one or more polymers. The biocompatible polymer may be biodegradable, non-biodegradable or a combination of biodegradable and non-biodegradable. The term "biodegradable" as used herein is defined to include both bioabsorbable and bioresorbable materials.

Figure 2:
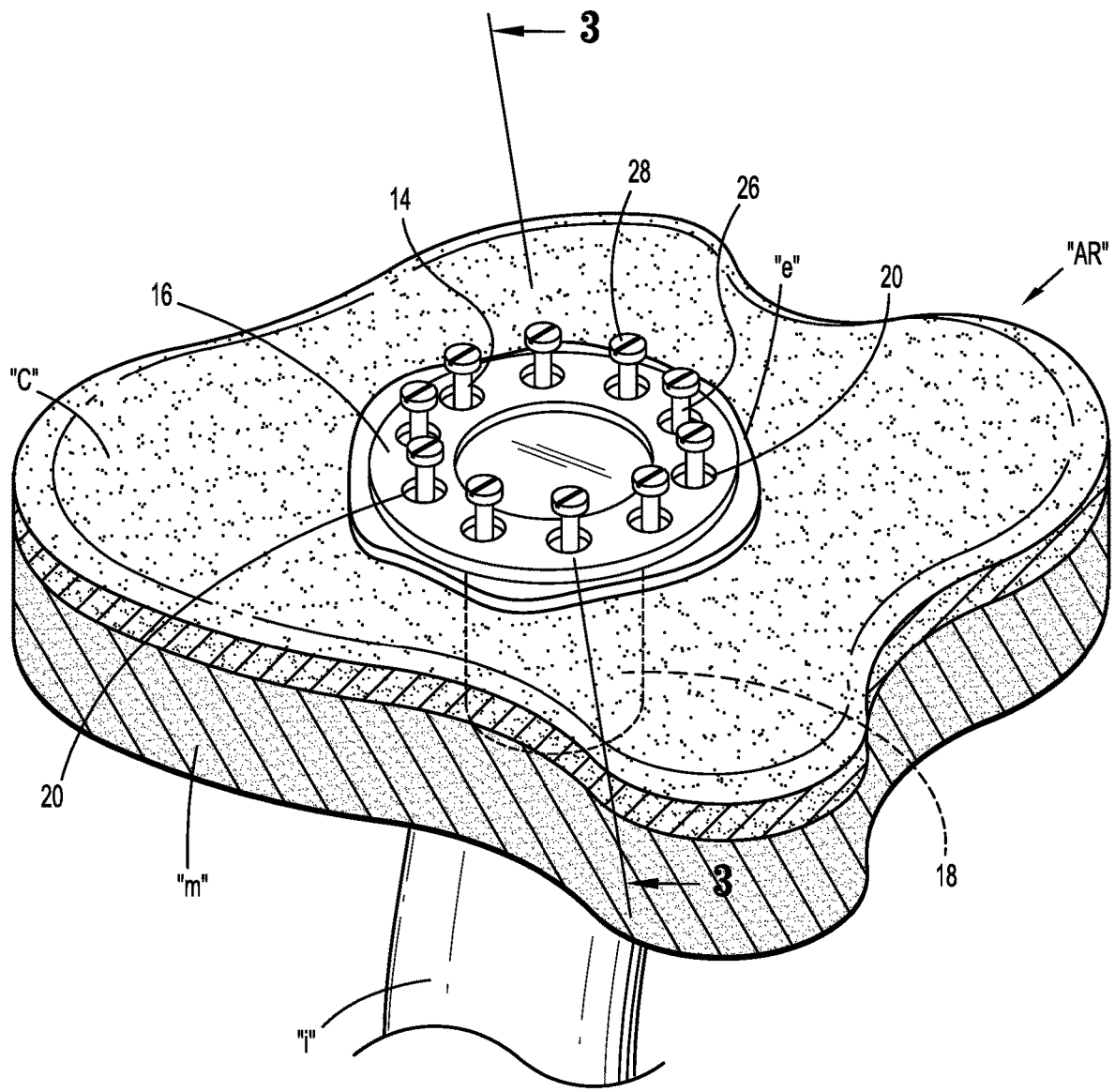
FIG. 2 is a perspective view similar to the view of FIG. 1 illustrating the flange segment of the guide engaging the end margins of the intestine and the insert segment of the guide at least partially positioned within the intestine with the fasteners disposed within the apertures of the flange segment.
Figure 3:
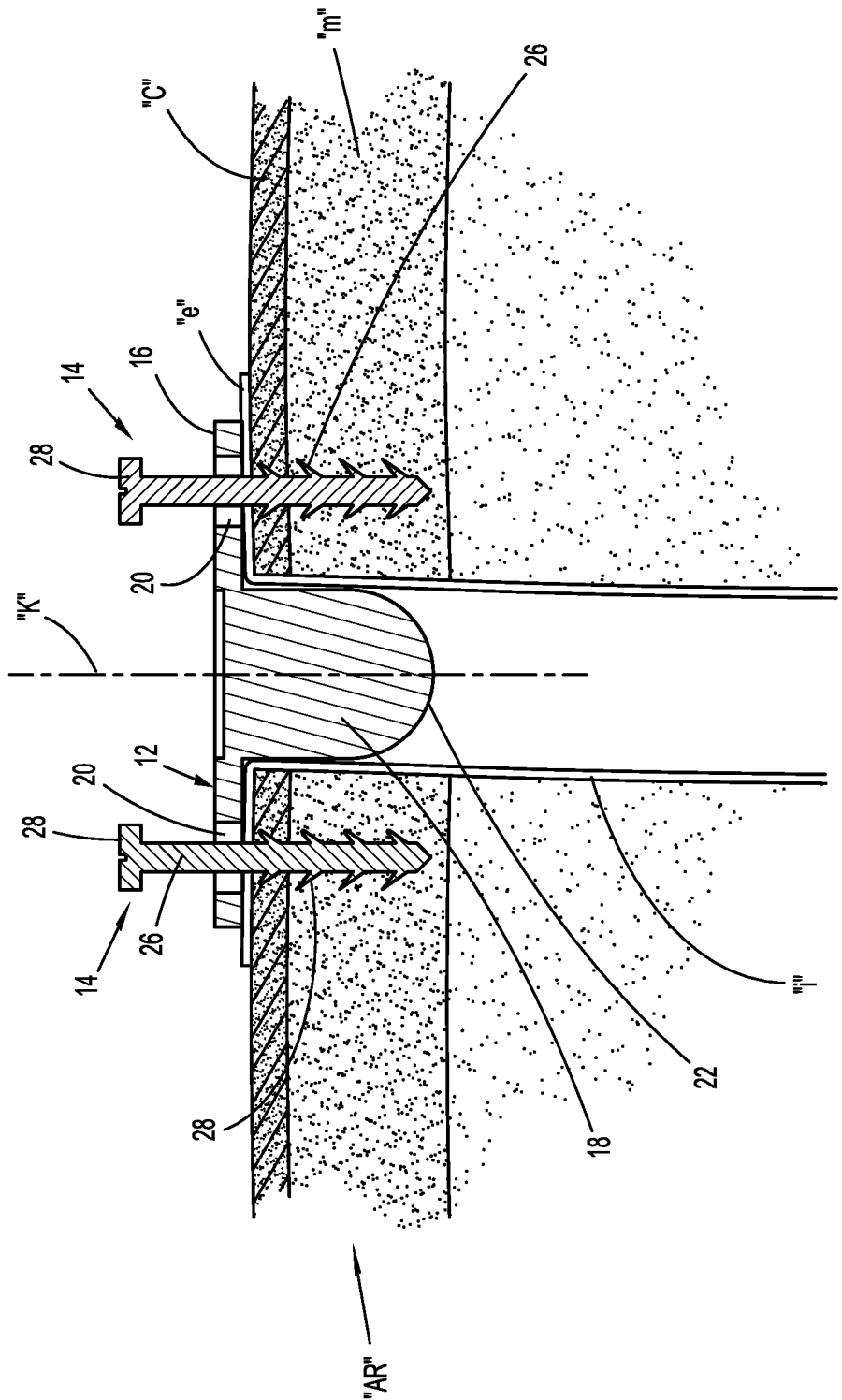
FIG. 3 is a cross-sectional view taken along the lines 3-3 of FIG. 2.

FIGS. 2-3 illustrate the guide 12 positioned relative to the abdominal region "AR" with the insert segment 18 introduced through the lumen of the intestine "i" (in phantom) and with the flange segment 16 engaging the end margins "e" of the intestine "i". In FIGS. 2 and 3, the fasteners 14 are at least partially advanced within the apertures 20 of the flange segment 16 with the fastener segments 26 of the fasteners 14 penetrating the end margins "e", the cutaneous tissue "c" and the muscle tissue "m". As depicted, the apertures 20 of the flange segment 16 of the guide 12 position the fasteners 14 evenly about the end margins "e" while the insert segment 18 maintains the patency of the intestine "i". The rounded entry end 22 facilitates passage and entry within the lumen of the intestine "i". The barbs 28 assist in securing the fasteners 14 relative to the guide 12.

The fasteners 14 may be delivered through the apertures 20 of the guide 12 to penetrate the end margins "e", the cutaneous tissue "c" and the muscle tissue "m" via any conventional methodology including manual application or with the use of a surgical instrument adapted to individually advance fasteners into tissue. Suitable instruments for application of the fasteners 14 are disclosed in commonly assigned U.S. Patent Publication Nos.: 2014/0121684 to Criscuolo and 2014/0276972 to Abuzaina et al., the entire contents of each disclosure being incorporated by reference herein.

Figure 4:
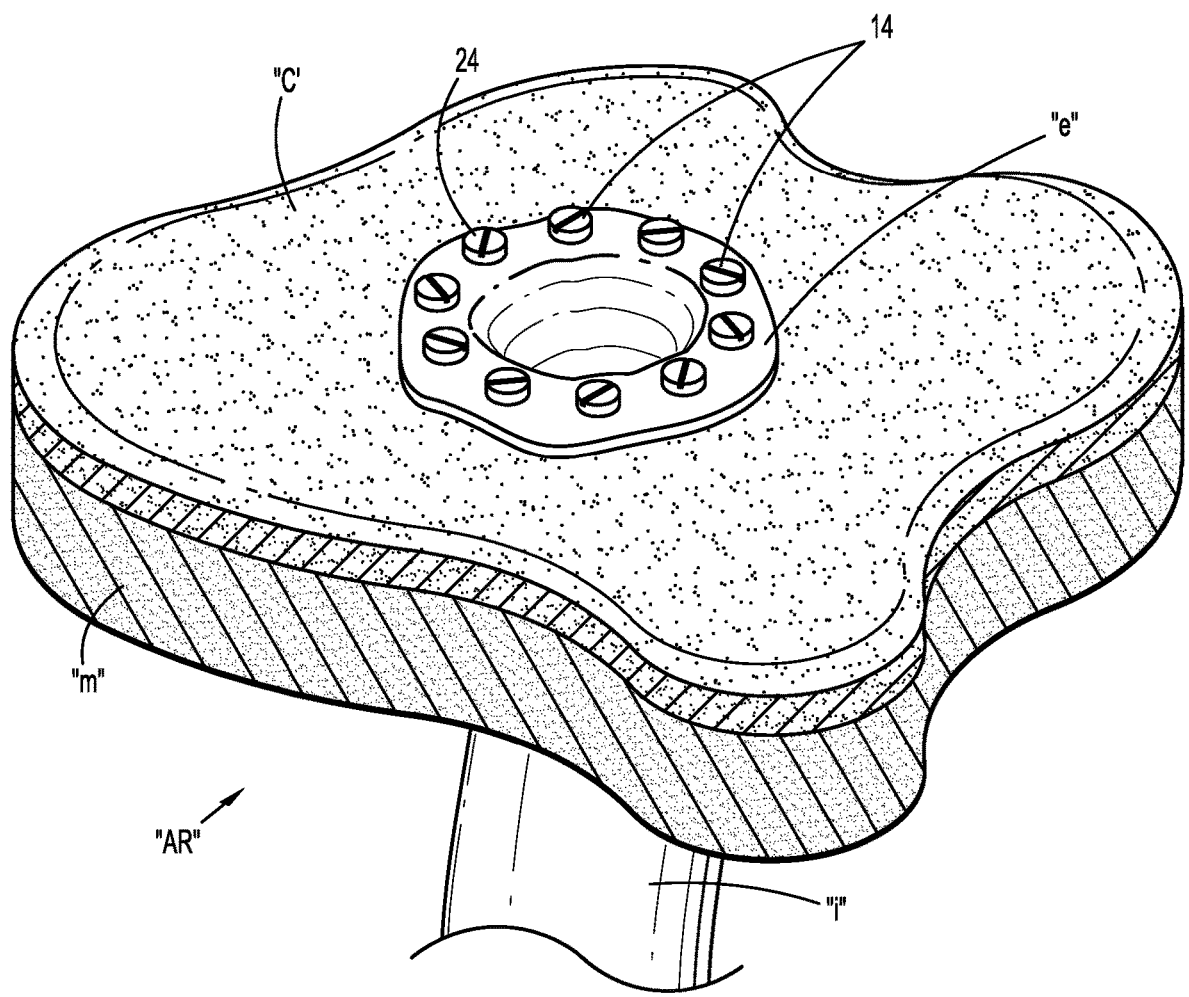
FIG. 4 is a view similar to the view of FIG. 2 illustrating the guide removed and the fasteners securing the end margins of the intestine to the abdominal tissue.

FIG. 4 illustrates the fasteners 14 fully advanced within the end margins "e" thereby securing the end margins "e" to the cutaneous tissue "c" and, possibly, the muscle tissue "m" to create a stoma, either temporary or permanent, in conjunction with the colostomy procedure. In FIG. 4, the guide 12 is removed which is effected by withdrawing the guide 12 from the stoma whereby the head segments 24 of the fasteners 14 pass through the apertures 20 of the flange segment 16 while the insert segment 18 exits the lumen of the intestine "i" and the newly formed stoma.

In embodiments, the guide 12 may be absorbable in whole or in part. For example, the flange segment 16 and/or the insert segment 18 may be formed of a biodegradable material. With this arrangement, the flange segment 16 may be left secured relative to the end margins "e", and eventually be absorbed within the tissue after a predetermined period of time. It is also envisioned that the insert segment 18 may be detachably connected to the flange segment 16 to permit removal of the insert segment 18 after attachment to the abdominal tissue leaving the flange segment 16 secured relative to the abdominal tissue.

Figure 5:
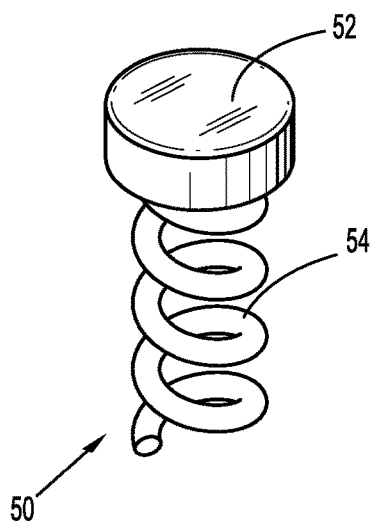
FIGS. 5-6 are perspective views of various embodiments of fasteners for use with the guide apparatus.
Figure 6:
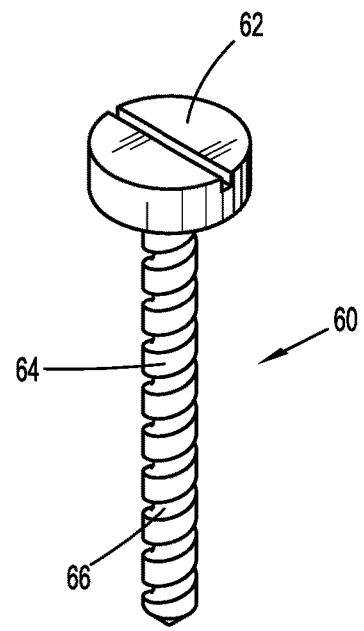

FIGS. 5-6 illustrate alternate embodiments of fasteners for use with the guide 12. The embodiment of FIG. 5 includes a fastener 50 having a head segment 52 and an elongated fastener segment 54 in the form of a single coil or helix. FIG. 6 illustrates a fastener 60 including a head segment 62 and an elongated fastener segment 64. The fastener segment 64 may be solid and have a helical groove 66 in its external surface similar to a screw fastener. Each of the fastener segments 54, 64 of the respective fasteners 50, 60 exhibit enhanced retention characteristics within the abdominal tissue.

Figure 7:
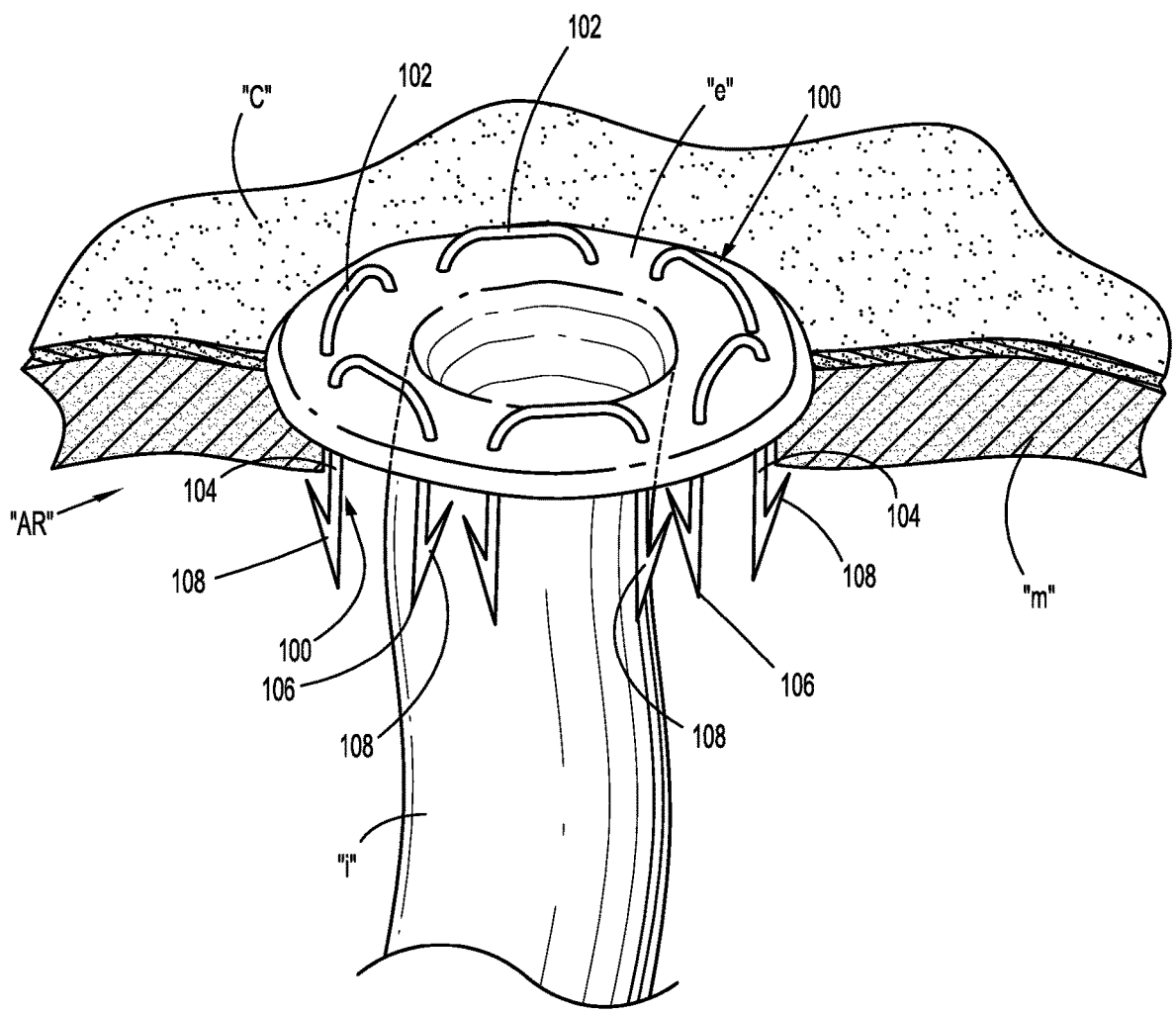
FIG. 7 is an alternate methodology for facilitating formation of a stoma within abdominal tissue illustrating the use of staples applied within the end margins of the intestine and the abdominal tissue.

FIG. 7 illustrates an alternate methodology for facilitating formation of a stoma in which staples 100 are applied to the end margins "e" of the intestine "i" to secure the end margins "e" to the cutaneous tissue "c" and, possibly, to the underlying muscle "m". In embodiments, the staples 100 are applied in an annular array and evenly spaced about the end margins "e" of the intestine "i" to provide a uniform connection of the end margins "e" to the cutaneous tissue "c" and muscle tissue "m". The staples 100 each include a backspan 102 and a pair of depending staple legs 104 with ends 106 which may or may not be pointed. The staple legs 104 may include barbs 108 or the like to assist in anchoring the staples 100 within the abdominal tissue. The staples 100 may be made in whole or in part of a biodegradable material. Any conventional methodology for delivering the staples may be utilized including manual and/or with the use of stapling instruments. The stapling instruments may individually apply the staples 100 with a skin stapler, e.g., as disclosed in commonly assigned U.S. Pat. No. 5,443,197 to Malis or simultaneously apply the staples 100 with a circular anastomosis instrument, e.g., as disclosed in commonly assigned U.S. Patent Publication No. 2015/0115015 to Prescott et al., the entire contents of each disclosure being hereby incorporated by reference herein.

Figure 8:
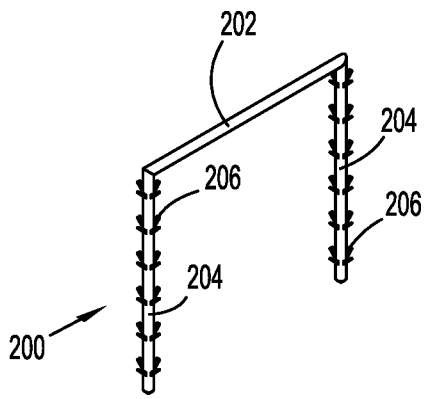
FIGS. 8-9 are views of an alternate embodiment of a staple for use with the methodology of FIG. 7.
Figure 9:
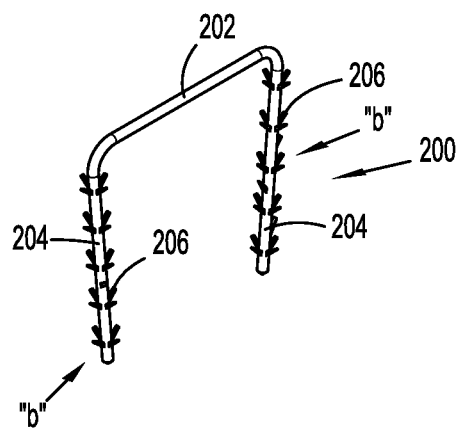

FIGS. 8-9 illustrate an alternate embodiment of a surgical staple for use with the methodology depicted in FIG. 7. In this embodiment, the staple 200 includes a backspan 202, a pair of staple legs 204 depending from the backspan 202 and having a plurality of circumferential barbs 206 spaced along each staple leg 204. In FIG. 8, the staple legs 204 are shown in their normal condition. FIG. 9 depicts the staple legs 204 compressed slightly radially inwardly in the direction of directional arrows "b". This may be effected manually or during delivery by the surgical stapler instrument. Upon application to the end margins "e", the cutaneous tissue "c" and the muscle tissue "m", the staple legs 204 are released from the stressed condition to assume the normal condition of FIG. 8 thereby driving the staple legs 204 and the circumferential barbs 206 radially outwardly into the abdominal tissue. This facilitates securement of the staples 200 relative to the engaged tissue.

Figure 10:
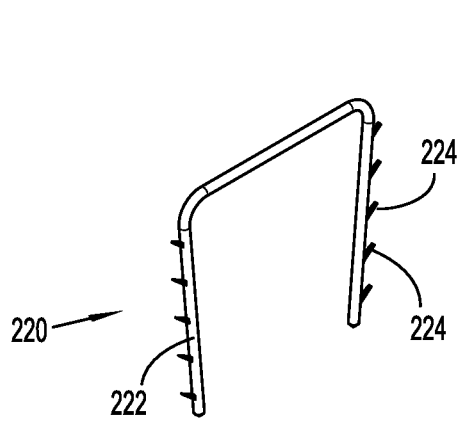
FIGS. 10-11 are views of additional alternate embodiments of staples for use with the methodology of FIG. 7.
Figure 11:
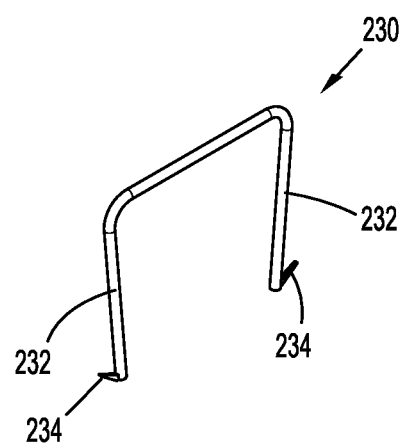

FIGS. 10-11 illustrate additional embodiments of a staple for use with the methodology of FIG. 7. FIG. 10 includes a staple 220 having staple legs 222 and a plurality of spaced anchors 224 on each staple leg 222. FIG. 11 illustrates a staple 230 having staple legs 232 each with a single anchor 234 at the end of the staple legs 232. The anchors 234 may be rigid or flexible. The respective staples 220, 230 of FIGS. 10-11 are shown in a compressed state with their staple legs 222, 232 slightly compressed radially inwardly. Upon application, the staple legs 222, 232 are released to engage the tissue in a similar manner discussed hereinabove in connection with the embodiment of FIGS. 8-9.

Figure 12:
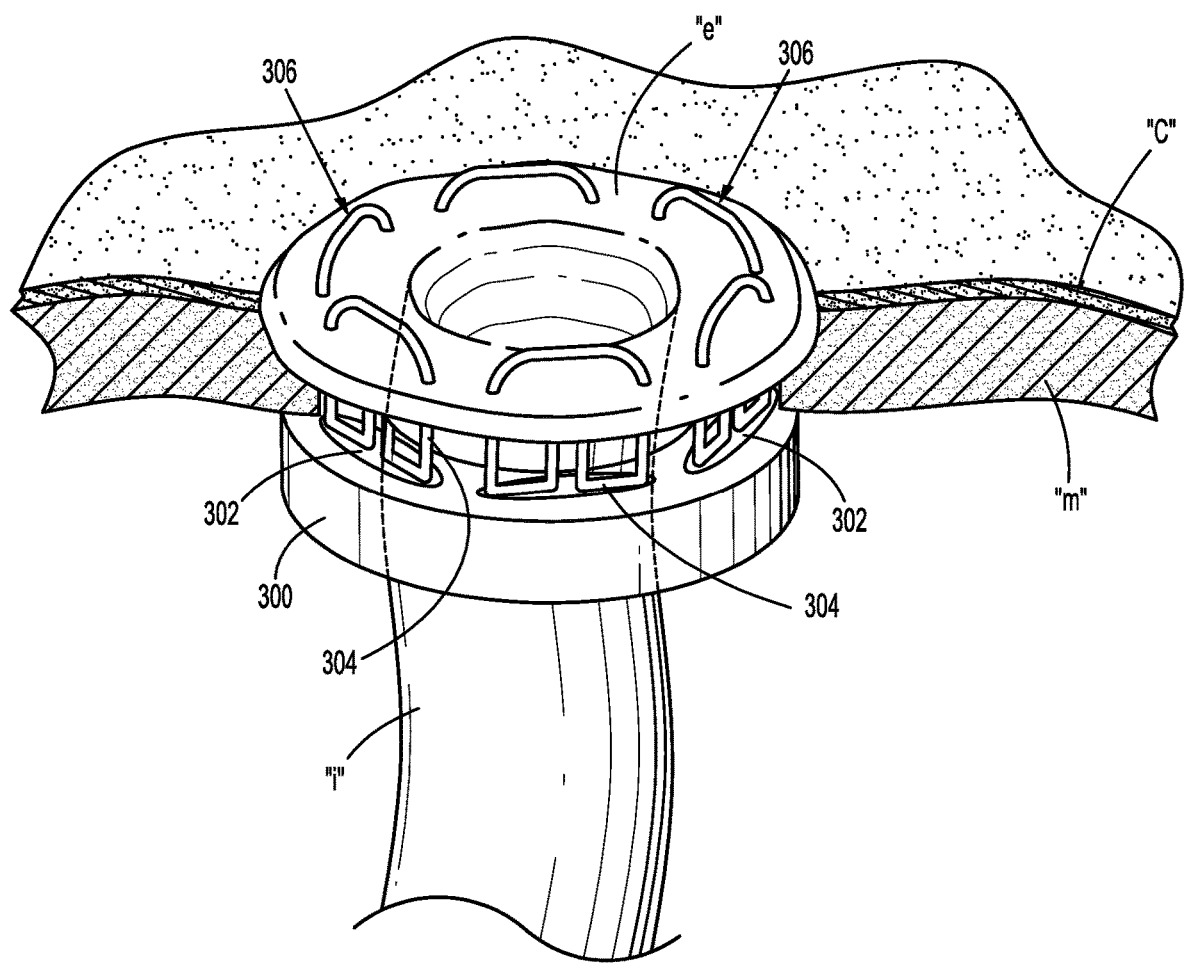
FIG. 12 is another alternate methodology for facilitating formation of a stoma within abdominal tissue illustrating the use of an anvil for clinching the staples within the end margins of the intestine and the abdominal tissue.

FIG. 12 illustrates another embodiment of a methodology for facilitating formation of a stoma in connection with a colostomy procedure. In this embodiment, an anvil ring 300 is positioned beneath at least the cutaneous tissue "c" and, optionally, the muscle tissue "m", in circumscribed relation about the intestine "i", and aligned with the end margins "e" of the intestine "i". The anvil ring 300 may include a plurality of recesses or pockets 302 which engage staple legs 304 of a staple or clip 306 to bend the staple legs 304 into a general "B"-shape within the abdominal tissue. A stapling instrument such as the circular, or an end-to-end anastomosis stapling instrument, identified hereinabove, may be positioned in registration with the end margins "e". The stapling instrument may be actuated to deliver an annular array of staples 306 through the end margins "e", cutaneous tissue "c" and muscle tissue "m" whereby the staple legs 304 of the staples 306 are crimped or bent within the pockets 302 of the anvil ring 300. Subsequent to securing the end margins "e" and creation of the stoma, the anvil ring 300 may be removed.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A guide apparatus for facilitating formation of a stoma, comprising:
    a guide including:
        an outer flange segment arranged about a central longitudinal axis, the flange segment configured for engaging end margins of a body vessel extending through an opening in skin of a subject, the flange segment defining a plurality of apertures; and
        an insert segment extending from the outer flange segment, the insert segment configured for at least partial positioning within the body vessel to maintain a patency of the body vessel; and
    a plurality of fasteners for insertion within respective apertures of the flange segment of the guide, the fasteners configured for penetrating the end margins extending through the opening in the skin to attach the end margins to the skin to thereby create a stoma.

2. The apparatus according to claim 1 wherein the fasteners each include a head segment and an elongated fastener segment depending from the head segment, the head segments each defining a cross-sectional dimension less than a corresponding cross-sectional dimension of the apertures of the flange segment of the guide to permit the guide to be removed subsequent to application of the fasteners through passage of the head segments through the apertures.

3. The apparatus according to claim 1 wherein the fasteners are arranged within the flange segment whereby adjacent fasteners are in equidistant spaced relation.

4. The apparatus according to claim 1 wherein the fasteners each include anchoring structure configured to facilitate securement of each fastener to the end margins of the body vessel and the skin.

5. The apparatus according to claim 1 wherein the fasteners are one of an elongated pin, a tack or a staple.

6. The apparatus according to claim 5 wherein the fasteners comprise a biodegradable material.

7. The apparatus according to claim 1 wherein the insert segment of the guide is separable from the flange segment.

8. The apparatus according to claim 7 wherein at least the flange segment of the guide comprises a biodegradable material.

9. A method for facilitating formation of a stoma, comprising:
    accessing an intestine through an opening in skin of a subject;
    positioning end margins of the intestine against the skin surrounding the opening;
    applying a flange segment of a guide against the end margins of the intestine; and
    delivering fasteners through apertures extending through the flange segment of the guide to secure the end margins of the intestine to the skin and create a stoma.

10. The method according to claim 9 including introducing an insert segment of the guide into the intestine to maintain a patency of the intestine.

11. The method according to claim 10 including removing the guide.

12. The method according to claim 11 wherein the fasteners each include a head segment and an elongated fastener segment depending from the head segment, the head segments each defining a cross-sectional dimension less than a corresponding cross-sectional dimension of the apertures of the flange segment of the guide whereby, during removing the guide, the head segments of the fasteners pass through the apertures of the flange segment of the guide.

* * * * *